United States Patent [19]
Kenkare et al.

[11] 3,974,270
[45] Aug. 10, 1976

[54] PRESSURIZED COMPOSITION FOR THE PRODUCTION OF A DRY SPRAY OF MILD BUT EFFECTIVE NON-STAINING ANTIPERSPIRANT

[75] Inventors: Divaker B. Kenkare, South Plainfield; Marius R. Moran, Hillsborough, both of N.J.

[73] Assignee: Colgate-Palmolive Company, New York, N.Y.

[22] Filed: Nov. 3, 1972

[21] Appl. No.: 303,574

[52] U.S. Cl. .................................. 424/47; 424/65; 424/66; 424/67; 424/68
[51] Int. Cl.² ........................................... A61K 7/38
[58] Field of Search ............................ 424/46, 47

[56] References Cited
FOREIGN PATENTS OR APPLICATIONS

| | | | |
|---|---|---|---|
| 779,899 | 8/1972 | Belgium | 424/47 |
| 2,035,901 | 12/1970 | France | 424/47 |
| 7,103,689 | 9/1971 | Netherlands | 424/47 |

*Primary Examiner*—Dale R. Ore
*Attorney, Agent, or Firm*—Herbert S. Sylvester; Murray M. Grill; Norman Blumenkopf

[57] ABSTRACT

A dry aerosol antiperspirant spray composition based on particulate aluminum chlorhydrate as the active antiperspirant, with a propellant fluid to maintain pressure in a container and to aid in discharging the antiperspirant composition from it through a dispensing valve, includes a water soluble poly-lower alkoxylated cetyl alcohol, such as cetyl propoxylate of 5 to 15 propoxy groups per mole, to act as a vehicle for the aluminum chlorhydrate and to diminish any irritation of the skin and staining of clothing resulting from contact with the aluminum chlorhydrate or a reaction product thereof, perspiration and oily materials in the composition or on the skin.

5 Claims, No Drawings

PRESSURIZED COMPOSITION FOR THE PRODUCTION OF A DRY SPRAY OF MILD BUT EFFECTIVE NON-STAINING ANTIPERSPIRANT

This invention relates to pressurized antiperspirant compositions which are dispensable from valved aerosol containers and are deposited on the skin in powder form. More particularly, it relates to such compositions based on aluminum chlorhydrate as the active antiperspirant ingredient and containing a water soluble poly-lower alkoxylated cetyl alcohol which helps to make the product non-staining and milder to the skin.

Aluminum chlorhydrate is today the most popular and most effective of the common antiperspirants in wide-scale use. It has been found that this astringent material, which is substantially insoluble in liquefied gas and other normally employed aerosol composition propellants, is at least partially dissolved and actuated when brought into contact with moisture. Therefore, it can be included in essentially anhydrous antiperspirant compositions which become activated upon been brought into contact with such moisture, e.g., perspiration, on the human skin.

Because a dry powdered astringent expelled under pressure onto the human skin does not adhere satisfactorily to it a vehicle is often present with the finely divided aluminum chlorhydrate so as to hold to it and help to maintain the powder on the skin after contact therewith. Such vehicles have usually been lipophilic materials which exhibit very little water solubility. These sometimes "insulate" the aluminum chlorhydrate from contact with moisture on the skin and thereby delay the onset of astringent action. Because exuded perspiration becomes malodorous very quickly it is desirable to accelerate the dissolving of the aluminum chlorhydrate, rather than to delay this action. Yet, it remains important to hold the powdered chlorhydrate onto the skin.

To promote dissolving of the chlorhydrate and any hydration and hydrolosis that results, water soluble vehicles may be employed. Such materials include nonionic surface active agents but in some cases it is found that the presence of such materials, in conjunction with the aluminum chlorhydrate, has an irritating effect on the skin of some users. Additionally, some fatty and oily materials from sebum or perspiration and sometimes from compositions applied to the skin may also be irritants and can cause staining of clothing contacted by the present astringent compositions. It is desirable to alleviate such irritating effects and to make the stains readily removable and completely to avoid them, if possible. The present invention promotes the solubilization of aluminum chlorhydrate and increases the mildness of the composition, tending to counteract irritating effects due to the astringent and any by-products thereof, e.g., hydrochloric acid, while simultaneously acting as a useful vehicle for applying the aluminum chlorhydrate to the skin from a pressurized aerosol powder composition and making the product non-staining. Any minor fatty or oily deposits are readily removed in washing due to the presence with them of the particular poly-lower alkoxylated cetyl alcohol utilized in the compositions of this invention.

In accordance with the present invention there is provided a composition in a pressurized container for the production of a dry spray of mild but effective non-staining antiperspirant which comprises aluminum chlorhydrate in a proportion sufficient to have an effective antiperspirant action, a poly-lower alkoxylated cetyl alcohol in proportion to act as a vehicle for the aluminum chlorhydrate and to diminish irritation of the skin and staining of clothing resulting from contact with the aluminum chlorhydrate or a reaction product thereof, perspiration and oily materials, and a propellant fluid to maintain pressure in the container and to aid in discharging the antiperspirant composition therefrom. In preferred embodiments of the invention the aluminum chlorhydrate is in finely divided powder form with particles in the 2 to 100 micron range, the poly-lower alkoxylated cetyl alcohol is polypropoxylated cetyl alcohol of about 10 propoxy groups per mole, the propellant fluid is a mixture of Propellants 11 and 12 with Propellant 11 being present in major proportion thereof and there are included in the composition a lower aliphatic ester of a higher fatty acid, such as isopropyl palmitate, a lower alkanol such as ethanol and a pyrogenic colloidal silica, such as that of particle sizes in the 0.1 to 2 micron range, sometimes sold under the trademark Cab-O-Sil.

Aluminum chlorhydrate, also sometimes called aluminum chlorohydroxide, is a standard article of commerce of the formula $Al_2(OH)_5Cl.2H_2O$ and is available in finely powdered form, suitable for dispensing through the small valve openings of aerosol spray dispensers. Of course, it may be size-reduced as desired. For the present applications particles of the aluminum chlorhydrate will be small, usually of about 1 to 1,000 microns, preferably 2 to 100 microns and most preferably averaging about 10 to 50 microns in diameter or equivalent diameter.

To suspend the aluminum chlorhydrate in particulate form and to produce a pressure in a dispensing container sufficient to discharge the aluminum chlorhydrate particles when desired there is utilized a propellant fluid, preferably a lipophilic material in which aluminum chlorhydrate is insoluble or only slightly soluble. Among the propellant fluids that are preferably used are the liquefied gases, materials which at atmospheric temperature and pressure will usually be in the gaseous state or can be vaporized readily at body temperature. Preferred useful propellants are liquefied gases or mixtures thereof of the hydrocarbon and/or halohydrocarbon types, preferably of 1 to 4 carbon atoms, with the halohydrocarbons having chlorine and/or fluorine as the halogen(s) thereof. Particularly useful are the mixtures of Propellants 11 and 12 (trichlorofluoromethane and dichlorodifluoromethane, respectively), as for example those in which the proportion is approximately 2:1 or 65:35. However, other liquefied gas propellants of the hydrocarbon and halogenated hydrocarbon types may also be employed in desired ratios to yield the dispensing pressure, which is normally from 10 to 100 lbs./sq. in., preferably 20 to 70 lbs./sq. in., more preferably 30 to 60 lbs./sq. in. and often ideally about 50 lbs./sq. in. Such pressures are given at 25°C. (room temperature). Among the propellants which may be employed are chlorodifluoromethane; dichlorodifluoromethane; difluoroethane; chlorodifluoroethane; dichlorotetrafluoroethane; (asymmetrical); dichlorotetrafluoroethane (symmetrical); chlorotrifluoroethane; dichlorofluoromethane; trichlorofluoromethane; dichloromethane; trichlorofluoroethane; "Chlorothene" ($CCl_3.CH_3$); and octafluorocyclobutane; all of which are examples of halogenated hydrocarbon propellants. Among the hydrocarbon propellants may be mentioned propane; 2-methyl propane (isobutane); n-butane and cyclobutane. Other such propellants are discussed in the text *Pressurized Packaging (Aerosols)* by Herzka and Pickthall (1958, Academic Press Inc., New York) at pages 19–77. Although it is highly preferable to utilize the liquefied gases and compatible lipophilic solvents which are vaporizable at human skin temperature, one may also employ the compressed gases, e.g., nitrous oxide, carbon dioxide, nitrogen, preferably in mixture with a liquefied gas or gases. The liquid propellants are preferred because they help to hold the aluminum chlorhydrate in desired suspension and facilitate its being carried through valve restrictions during discharge.

With the aluminum chlorhydrate-propellant fluid mix there is present a poly-lower alkoxylated cetyl alcohol vehicle in sufficient proportion to help the aluminum chlorhydrate powder being dispensed to adhere to the skin area against which it is directed. The poly-lower alkoxylated cetyl alcohol will have such a lipophilic-hydrophilic balance as to be water soluble and promote activation of the aluminum chlorhydrate when it is on moist skin. Thus, when perspiration contacts the aluminum chlorhydrate particles coated with poly-lower alkoxylated cetyl alcohol (or the mix of aluminum chlorhydrate and fumed silica particles coated with a mixture of hydrophilic poly-lower alkoxylated cetyl alcohol and higher fatty acid ester of lower alcohol) the alkoxylated material dissolves, and because of its hydrophilic and surface active properties promotes the contact of the aluminum chlorhydrate with moisture and the consequent activation of the astringent product. Additionally, the poly-lower alkoxylated cetyl alcohol helps to remove greasy and oily stains from garments contacted with the present astringent compositions, when such garments are washed. It has a soothing effect and counters irritation which may be caused to some sensitive skins by the presence of the aluminum chlorhydrate or reaction products thereof or by the presence of perspiration, oily materials and other constituents of compositions applied to the skin.

The poly-lower alkoxylated cetyl alcohol is usually alkoxylated by propylene oxide but may have ethylene oxide present, too. The extent of alkoxylation will generally be within the range of 3 to 100 lower alkoxy groups per mole (lower meaning 2- to 3- carbon alkoxy groups) and of these, 10 to 100% will normally be propoxy, rather than ethoxy. The propoxy may be n-propoxy or isopropoxy, with the latter being more common. Preferred poly-lower alkoxylated cetyl alcohols will be completely water soluble and will contain from 3 to 20 alkoxy groups per mole, often 5 to 15 and most preferably about 10 propoxy groups per mole. However, a balance can be struck betwee the proportion of ethoxy and propoxy groups and the length of the poly-lower alkoxy chain to produce a product of the most desired hydrophilic, water soluble, counter-irritant, detersive and vehicle properties.

To help to hold the aluminum chlorhydrate particles intimately suspended in the propellant - poly-lower alkoxylated cetyl alcohol solution (the alkoxylated alcohol is sufficiently propellant-soluble so as not to settle out, on standing) a finely divided silica is very preferably present. Such material also assists in maintaining a uniform coating of the chlorhydrate on the skin an sorbs any excess perspiration not taken up by the chlorhydrate particles; yet it releases such perspiration to the chlorhydrate to promote activation thereof.

For best results the finely divided silica is a colloidal silica, preferably of the pyrogenic type, having a particle size in the 0.1 to 10 micron range, preferably of 0.1 to 2 microns. Such products are available under the tradename Cab-O-Sil, such as Cab-O-Sil M-5. Of course, equivalents or substitutes may be employed providing that they are of similar satisfactory properties.

With the hydrophilic polyalkoxylated cetyl alcohol it is desirable to employ a lesser quantity of a lipophilic vehicle to help to hold the astringent on the skin and to facilitate a uniform distribution thereof. Vehicles of such desired properties are the lower aliphatic alcohol esters of higher fatty acids. The lower aliphatic alcohols thereof will usually be of 1 to 4 carbon atoms and the higher fatty acids are normally of 12 to 18 carbon atoms. More preferably, the alcohols will be of 2 to 3 carbon atoms and the higher fatty acids will be of 14 to 18 carbon atoms. Most preferably, the alcohol is isopropanol and the fatty acid is palmitic acid. Thus, it is noted that the lipophilic portions of both vehicles will be of 16 carbon atoms in the most preferred embodiments of the invention.

It is usually desirable and sometimes very important to have a co-solvent present in the composition in minor proportion to help to keep the lipophilic and hydrophilic vehicles uniformly distributed and to assist in maintaining them in such form that they are readily dispensed from the pressurized container when the valve thereof (it usually has a very small clearance) is opened. Further, it is desirable that a small proportion of volatilizable hydrophilic component be applied to the skin to help vaporize off from the skin upon contact some moisture which may be present thereon. This gives a very slight cooling effect which assures that the user will have a signal that the desired skin surface areas have been sufficiently covered with antiperspirant composition. A useful co-solvent having the mentioned properties is a lower aliphatic alcohol, usually of 1 to 4 carbon atoms, preferably of 2 to 3 carbon atoms and most preferably, ethanol. Although ethanol is highly preferred, isopropanol may be employed, too, as may be methanol and isobutanol, generally in smaller quantities. The ethanol may be denatured but it is preferable that it be essentially water free, as is also preferable for the entire composition. While it is normal for ethanol to include about 5% of water, it is preferred that the present compositions contain no water at all and at the most no more than 1% thereof, with best efforts being made to limit this to 0.1%.

Various adjuvants may be present with the astringent or antiperspirant compositions. Among these may be included bactericides, e.g., hexachlorophene, in permissible quantities; colorants, e.g., approved F. D. dyes and pigments, perfumes, e.g., synthetic musks, natural odorants, natural and synthetic floral perfumes; solvents, e.g., hydrocarbon oils, ethers; supplemental astringents, e.g., aluminum, zirconium and zinc salts, such as aluminum chloride; and nonionic surface active agents, e.g., nonyl phenyl polyoxyethylene ethanol of ten oxyethylene groups per mole. Of course, such materials will be present only in proportions that are compatible with the other constituents and often none of these will be utilized except perfumes or odorants.

The proportions of the pressurized composition components employed are such as to result in the production of a dry spray of mild but effective non-staining antiperspirant. The aluminum chlorhydrate should be present in sufficient proportion to produce effective antiperspirant action and the propellant should be of the desired pressure and in such state as to suspend the aluminum chlorhydrate effectively for free discharge. The polylower alkoxylated cetyl alcohol acts as a vehicle in the proportions utilized and helps to diminish any irritation of the skin and staining of the clothing which might result from contact with the aluminum chlorhydrate, a reaction product thereof, perspiration or oily materials present. Generally the proportion of aluminum chlorhydrate is from 2 to 7%, preferably 2 to 4% and most preferably about 3% of the composition in the pressurized container. The propellant will usually be from 80 to 95% of the composition, preferably from 85 to 93% thereof and most preferably should be about 90%. The poly-lower alkoxylated cetyl alcohol is normally 2 to 9% of the composition, preferably 3 to 7% and most preferably about 3.8% thereof. The pyrogenic silica will usually be from 0.1 to 2%, preferably 0.2 to 1% and most preferably about 0.4% of the antiperspirant composition and the auxiliary vehicle, such as a lower aliphatic alcohol ester of higher fatty acid, is from 0.5 to 3%, preferably from 0.5 to 1.5% and most preferably about 1% of the composition. The solvent, preferably a lower alkanol or a mixture thereof, generally constitutes from 0.5 to 5% of the composition, preferably 1 to 3% thereof and most preferably about 1.8%. The various adjuvants that may be employed can total up to as much as 20% of the product, especially when an auxiliary solvent is present, but generally will be limited to 10% thereof and preferably to 5%, with individual adjuvants usually being limited to 2% and preferably to 1% of the composition.

The present compositions are well dispersed and may be characterized as homogeneous, requiring little agitation before use to make certain that the proportion of astringent is constant during dispensing. The aluminum chlorhydrate particles adhere well to the skin onto which they are sprayed and the astringent is readily activated by contact with moisture on the skin. The products are non-staining and are mild to the skin with no irritation being noted. The effects described are attributable to the use of the particular poly-lower alkoxylated cetyl alcohol vehicles in conjunction with the aluminum chlorhydrate and, in preferred embodiments, with the auxiliary solvent, vehicle and dispersing aid. When other higher fatty alcohols than cetyl alcohol are poly-lower alkoxylated the results obtained are not as satisfactory as those of the present invention and such is also the case when other astringents than the aluminum chlorhydrate are employed. Similarly, when the higher fatty esters of lower alcohols are esters of fatty acids outside the ranges given (best results are obtained with the 16 carbon fatty acid) poor effects are obtained and when solvents and propellants other than those mentioned are used or when the alcohol solvent is omitted the products are not as good. Thus, it appears that the coaction of the mentioned ingredients is an important feature for the obtaining of the desired results mentioned.

The following examples illustrate but do not limit the invention. Unless otherwise mentioned, all parts are by weight and all temperatures are in °C.

EXAMPLE 1

| | Parts by weight |
|---|---|
| Aluminum chlorhydrate (powdered, of particle sizes in the 2 to 100 micron range, averaging about 10 microns) | 3.0 |
| Polypropoxylated cetyl alcohol (Procetyl AWS, mfd. by Croda, Inc.) | 3.8 |
| Pyrogenic silica (of particle sizes in the 0.1 to 2 micron range, sold as Cab-O-Sil M-5 by Cabot Corporation) | 0.4 |
| Isopropyl palmitate | 1.0 |
| Denatured ethyl alcohol (SD No. 40, anhydrous) | 1.8 |
| Perfume | 0.2 |
| Propellant mixture, 65:35 Propellant 11: Propellant 12 (Freons 11 and 12) | 89.8 |

The above composition is made by adding each of the constituents to a valved dispensing container capable of being pressurized through the valve thereof, sealing the can and then adding the propellant mixture to it under pressure through the valve so as to obtain a final pressure of 50 lbs./sq. in. The essentially anhydrous composition is packed and sent to storage. After storage periods of as long as three months the product is tested in vivo and in vitro and it is found that the spray characteristics are uniform or substantially uniform throughout the entire life of the product. In any cases where there may be some inequality of spraying characteristics a light shaking of the container before discharging the antiperspirant composition helps to suspend the aluminum chlorhydrate more evenly in the liquefied gas medium, together with the other parts of the composition, and produces the uniform spray characteristics desired.

When tested on human subjects (a panel of ten) it is found that the present composition is an efficient antiperspirant, significantly diminishing the amount of perspiration exuded (by proportions from 20 to 80%) and is non-irritating. Also, articles of clothing which come into contact with the areas to which the antiperspirant product is applied are not stained by it and any slight deposits of fatty or oily materials, astringent and hydrolysis products thereof are readily removed upon normal washing. In vitro tests verify these conclusions.

On the contrary, when the Procetyl AWS is replaced by isopropyl myristate the products tend to stain clothing and items of fabric onto which they are sprayed and such stains are not as readily removable during washing. Similarly, when aluminum chlorhydrate is replaced by aluminum sulfate in these formulas the product is more irritating to the skin. When Cab-O-Sil is omitted from the formula the dispensing container should be shaken more vigorously before use to produce an evenly dispensed product. If the isopropyl palmitate is omitted the product is still useful but it appears that the aluminum chlorhydrate does not adhere as well to the skin onto which the composition is sprayed.

When proportions of the various constituents are modified so as to be outside the ranges described in the specification various detrimental effects are noted. For example, when the amount of aluminum chlorhydrate is diminished to outside the range its effect as an astringent is decreased and when more is employed significantly shorter bursts of spray (harder to control) are required and in some cases irritation may be apparent.

When too much of the poly-lower alkoxylated cetyl alcohol and the isopropyl palmitate or similar ester is used the product may become sticky and may cause greasy staining of clothing whereas when too little of these materials is employed the chlorhydrate does not get held satisfactorily to the skin onto which it is directed. Similarly, when the proportions of lower alkanol and/or propellant are outside the desired ranges the utilities of these materials are diminished. However, when variations in the constituents are made within the ranges given acceptable products having the useful characteristics recited above are obtained.

EXAMPLE 2

| | Parts by weight |
|---|---|
| Aluminum chlorhydrate, powdered (with particle sizes of 2 to 100 microns) | 3.0 |
| Poly-lower alkoxylated cetyl alcohol (Procetyl AWS) | 6.5 |
| Cab-O-Sil M-5 | 0.4 |
| Perfume | 0.2 |
| Propellant mixture (65:35 Propellants 11:12) | 89.9 |

EXAMPLE 3

| | Parts by weight |
|---|---|
| Aluminum chlorhydrate powder, finely divided | 3.0 |
| Polypropoxylated cetyl alcohol (averaging ten propoxy groups per mole) | 4.5 |
| Pyrogenic silica, Cab-O-Sil of particle sizes of about 0.5 micron | 0.4 |
| Perfume | 0.2 |
| Propellant mixture (2:1 Freon 11:Freon 12) | 91.9 |

In the compositions of Examples 2 and 3, which produce excellent powdered antiperspirants dispensable from an aerosol container of the type described in Example 1, various modifications in proportions and constituents are made in accordance with the teachings in the preceding specification, with satisfactory antiperspirant compositions resulting. For example, in these formulations the polypropoxylated cetyl alcohol can be replaced with a corresponding alcohol containing from 30 to 60% of ethoxy groups, on a lower alkoxy molar basis, without interfering with the desirable activity of the composition. Also, the pyrogenic silica component is replaced by other colloidal silicas in the 0.1 to 10 range, preferably in the range of 0.1 to 2 microns, a wide variety of which is available on the market. Proportions of aluminum chlorhydrate are changed within the range of 2 to 7%, with the greater proportions being more actively astringent and antiperspirant, yet without irriation to normal skin. However, the aluminum chlorhydrate should not be changed to any known astringent. Also readily changeable without affecting the properties of the composition is the propellant mixture and any suitable combination of the propellants mentioned in the specification which yields a satisfactory dispensing pressure, usually from 10 to 100 lbs./sq. in. and preferably from 20 to 70 lbs./sq. in., at 25°C., is useful. For example, mixtures of propane and isobutane may be employed.

EXAMPLE 4

| | Parts by weight |
|---|---|
| Aluminum chlorhydrate powder (average particle size in the 10 to 40 micron range) | 6.0 |

EXAMPLE 4-continued

| | Parts by weight |
|---|---|
| Polypropoxylated cetyl alcohol (as described in Example 1) | 7.0 |
| Isopropyl palmitate | 1.0 |
| Denatured ethanol (anhydrous) | 1.8 |
| Cab-O-Sil M-5 | 0.4 |
| Perfume | 0.2 |
| Propellant mixture to generate 50 lbs./sq. in. at 25°C. (Propellants 11 and 12) | 83.6 |

As with the previous compositions, that of this example makes a satisfactory, adherent, long term effective, dry powdered antiperspirant, dispensable from a valved aerosol container. It is effective in diminishing perspiration and is non-irritating to normal skins. As is apparent from the increased content of astringent aluminum chlorhydrate, less of the composition needs to be sprayed onto the skin to obtain an effect equivalent to those of the previous examples.

The invention has been described with respect to illustrations and working examples thereof but is not to be considered as limited to them because it is evident that one of skill in the art with the present specification before him will be able to utilize substitutes and equivalents without departing from the spirit and scope of the invention.

What is claimed is:

1. A composition in a pressurized container for the production of a dry spray of mild but effective non-staining antiperspirant which consists essentially of from 2 to 7% of powdered aluminum chlorhydrate, said proportion being sufficient to have an effective antiperspirant action, from 2 to 9% of a polypropoxylated cetyl alcohol having from 3 to 100 propoxy groups, and from 80 to 95% of a propellant fluid to maintain pressure in the container and to aid in discharging the antiperspirant composition therefrom.

2. A composition according to claim 1 wherein the aluminum chlorhydrate is in particulate form with particles in the 1 to 1,000 micron range, the polypropoxylated cetyl alcohol is a completely water soluble polypropoxylate of 3 to 20 propoxy groups per mole and the propellant is a mixture of liquefied hydrocarbons, halohyrocarbons or both, which creates a pressure of from 20 to 70 lbs./sq. in. at 25°C.

3. A composition according to claim 2 which is essentially anhydrous and which includes as auxiliary constituents from 0.1 to 2% of pyrogenic colloidal silica of particle sizes in the 0.1 to 10 micron range, 0.5 to 3% of a lower aliphatic alcohol ester of a higher fatty acid of 12 to 18 carbon atoms, wherein the lower aliphatic alcohol is of 1 to 4 carbon atoms, and 0.5 to 5% of a lower alkanol of 1 to 4 carbon atoms.

4. A composition according to claim 3 comprising from 2 to 4% of particulate aluminum chlorhydrate of particle sizes in the 2 to 100 micron range, 3 to 7% of polypropoxylated cetyl alcohol of 5 to 15 propoxy groups per mole, 85 to 93% of a mixture of halogenated hydrocarbon liquefied gases of 1 to 4 carbon atoms wherein the halogens are selected from the group consisting of chlorine and fluorine, 0.2 to 1% of pyrogenic colloidal silica of particle sizes in the 0.1 to 2 micron range, 0.5 to 1.5% of a lower aliphatic alcohol ester of a higher fatty acid wherein the lower aliphatic alcohol is of 2 to 3 carbon atoms and the higher fatty acid is of 14 to 18 carbon atoms and 1 to 3% of a lower alkanol of 2 to 3 carbon atoms, at a pressure of from 30 to 60 lbs./sq. in. at 25°C.

5. A composition according to claim 4 comprising about: 3% of particulate aluminum chlorhydrate, of particle sizes in the 2 to 100 micron range, 3.8% of polypropoxylated cetyl alcohol of about 10 propoxy groups per mole, 90% of a mixture of trichlorofluoromethane and dichlorodifluoromethane in approximately 2:1 ratio, 0.4% of pyrogenic colloidal silica of particle sizes in the 0.1 to 2 micron range, 1% of isopropyl palmitate and 1.8% of anhydrous ethanol, at a pressure of about 50 lbs./sq. in. at 25°C., in a pressure-holding container equipped with a spray-dispensing valve.

* * * * *